United States Patent
Schierstedt

(12) 
(10) Patent No.: US 6,472,439 B1
(45) Date of Patent: Oct. 29, 2002

(54) MEDICINAL PLANT DRY EXTRACTS

(75) Inventor: Detlef Schierstedt, St. Augustin (DE)

(73) Assignee: Krewel Meuselbach GmbH, Eitorf (DE)

(*) Notice: Subject to any disclaimer, the term of this patent is extended or adjusted under 35 U.S.C. 154(b) by 0 days.

(21) Appl. No.: 09/581,828

(22) PCT Filed: Dec. 16, 1998

(86) PCT No.: PCT/EP98/08247

§ 371 (c)(1),
(2), (4) Date: Dec. 14, 2000

(87) PCT Pub. No.: WO99/32130

PCT Pub. Date: Jul. 1, 1999

(30) Foreign Application Priority Data

Dec. 19, 1997 (DE) .......................... 197 56 677
Mar. 28, 1998 (DE) .......................... 198 14 014

(51) Int. Cl.$^7$ .......................... A61K 47/32; A61K 9/48; A61K 9/20; A61K 9/46; A61K 9/50
(52) U.S. Cl. .................. 514/772.4; 514/772.5; 424/451; 424/464; 424/465; 424/466; 424/497
(58) Field of Search ................. 424/725, 400, 424/401, 408, 464, 466, 465, 451, 497, 752; 514/772.4, 772.5

(56) References Cited

U.S. PATENT DOCUMENTS

| | | | |
|---|---|---|---|
| 5,352,455 A | * 10/1994 | Robertson | 424/436 |
| 5,401,502 A | * 3/1995 | Wunderlich et al. | 424/195.1 |
| 5,447,729 A | * 9/1995 | Belenduik et al. | 424/490 |
| 5,942,244 A | * 8/1999 | Friedman et al. | 424/435 |

FOREIGN PATENT DOCUMENTS

| | | |
|---|---|---|
| DE | 4201172 | 7/1993 |
| EP | 0265338 | 4/1988 |
| EP | 0496705 | 7/1992 |
| EP | 0664131 | 7/1995 |
| EP | 0702957 | 3/1996 |
| EP | 0722719 | 7/1996 |
| WO | WO 90/03179 | 4/1990 |

OTHER PUBLICATIONS

H. Sucker et al., Pharmazeutische Technologie, G. Thieme, Verlag, Stuttgart, pp. 79–80 (1991).
B.C. Lippold et al., Pharm. Ind. 40, No. 5, pp. 541–549 (1978) (and English Abstract).
R. Voight et al., Lehrbuch der pharmazeutischen Technologie VEB Verlag, Berlin, p. 488 (1982).

* cited by examiner

Primary Examiner—Thurman K. Page
Assistant Examiner—Humera N. Sheikh
(74) Attorney, Agent, or Firm—Brobeck, Phleger & Harrison LLP

(57) ABSTRACT

The present invention relates to orally administerable medicinal plant dry extracts, wherein the non-volatile phase of the extract is bound in a microdisperse form and/or in the form of a semisolid or solid solution to a first carrier which is soluble in or miscible with alcohol, soluble in or miscible with water and solid at room temperature, optionally in addition to other auxiliaries and/or additives. Optionally, a second carrier is selected from carriers which are insoluble in alcohol, insoluble in water or swellable in water and solid at room temperature, or alkaline earth metal and/or alkali metal carbonates including hydrogencarbonates.

18 Claims, No Drawings

MEDICINAL PLANT DRY EXTRACTS

The present invention relates to orally administerable medicinal plant dry extracts.

EP 0 702 957 A relates to orally administerable Saint-John's-wort extracts and a process for their preparation. Polyvinyl pyrrolidone is added to Saint-John's-wort extracts, and the fluid phase is concentrated to dryness at elevated temperature and/or under vacuum. This results in an improved release of the dianthrones as compared to standard preparations.

EP 0 664 131 A relates to orally administerable kava fluid extracts and a process for their preparation. Kava fluid extracts are contacted with a carrier which is solid at room temperature and selected from polyvinyl pyrrolidone, cellulose derivatives and/or starch derivatives, and the fluid extract is concentrated to dryness at elevated temperature and/or under vacuum. This results in an improved release of the 6 main kavapyrones as compared to standard preparations.

The medical effects of medicinal plant dry extracts from sabalfructus (palmetto fruit), Passiflora, chaste-tree (*Vitex agnus-castus*), Crataegus, kava, ginkgo, nettle, holy thistle and/or Hypericum are known from the prior art.

DE 42 01 172 C1 relates to pellets containing Aloe vera extract formed by dispersion of the Aloe vera extract in a matrix which predominantly consists of a builder, namely collagen, gelatin, fractionated gelatin, a collagen hydrolysate and/or a gelatin derivative.

However, it is a common feature of conventional dry extracts, especially those which are commercially available, that the release of active substances, i.e., the speed and degree of release of the components, highly varies from batch to batch due to the natural substance character of the medicinal plants. Even competing products having the same extract declarations are often considerably different. The known pharmacopoeias also merely define the quantity of the components, but no properties which would be desirable for a reliable therapy with the extracts.

Therefore, it has been the object of the present invention to standardize medicinal plant dry extracts on a high level in terms of both degree and speed of release and thus to increase the safety of therapies.

In a first aspect of the present invention, the above object is achieved by orally administerable medicinal plant dry extracts, wherein the non-volatile phase of the extract is bound in a microdisperse form and/or in the form of a semisolid or solid solution to a carrier which is soluble in or miscible with alcohol, soluble in or miscible with water and semisolid or solid at room temperature, optionally in addition to other auxiliaries and/or additives.

In extracts of natural substances, which contain a wide variety of active components and other accompanying substances, it was not to be expected that such an inhomogeneous mixture of substances would be subject to much improvement of solubility in the mentioned carriers and thus to a standardization of release.

Surprisingly, it has been found that dissolving the carriers in a fluid extract yields an extract-carrier complex upon concentration in which the active components are bound in a microdisperse form and/or in the form of a semisolid or solid solution in such a way that the speed and degree of release of the active components could be standardized, with blending different batches, if necessary. The semisolid or solid extract phase is, in particular, a spissum or siccum phase which contains the active components.

The release of active substances from solid oral dosage forms can be determined, for example, according to the Deutsches Arzneibuch (German Pharmacopoeia) DAB 10 V5.4. When the release of the extracts using a medium which corresponds to the medium in the stomach was measured, a significantly improved release of the active components over the prior art was achieved.

Said carriers which are soluble in or miscible with alcohol, soluble in or miscible with water and semisolid or solid at room temperature (25° C.) are preferably selected from polyethylene glycols, especially those having a molecular weight of at least 1000, polyvinyl alcohols, polyvidone acetate and/or polyvinyl pyrrolidone.

Polyvinyl alcohol as used according to the present invention usually has a molecular weight of from 28,000 to 40,000. Polyethylene glycols having appropriate molecular weights of at least 1000, for example, 4000, are commercially available. The molecular weight determines the consistency at room temperature. Polyvinyl pyrrolidones are commercially available, for example, under the designation of "Kollidon®" with different molecular weights. The same applies to polyvidone acetates, which are available under the designation of "Kollidon VA".

In another embodiment of the present invention, the extracts further contain a second carrier selected from carriers which are insoluble in alcohol, insoluble in water or swellable in water and solid at room temperature, or alkaline earth metal and/or alkali metal carbonates including hydrogencarbonates.

The second carrier is preferably selected from carbonates, such as sodium hydrogencarbonate, calcium carbonate or magnesium carbonate, and water-swellable organic polymers, especially starch, starch derivatives, cellulose, cellulose derivatives; cross-linked cellulose derivatives being particularly preferred. Similarly, particularly preferred second carriers are cross-linked polyvinyl pyrrolidone derivatives which are commercially available, for example, under the designation of "Kollidon®Cl" or "Polyplastone". Thus, effervescent tablets or drinking tablets can also be prepared using disintegrants or effervescent agents per se known in the prior art.

It is particularly preferred according to the present invention if the weight ratio of the second carrier to the first carrier is from 30:1 to 1:1, more preferably from 10:1 to 3:1.

According to the present invention, the medicinal plants are preferably selected from sabalfructus (palmetto fruit), Passiflora, chaste-tree (*Vitex agnus-castus*), Crataegus, kava, ginkgo, nettle, holy thistle, Hypericum, valerian, Cimicifuga root or rootstock and/or Cynara.

The term "soluble in alcohol" as used herein means solubility in methanol, ethanol or 2-propanol, with heating, if necessary. Fluid extracts are often prepared using these solvents. Additionally, however, extraction with other solvents, such as acetone, acetone-water mixtures, or extraction with supercritical steam or carbon dioxide is also known. The term "solubility" is differently defined in different pharmacopoeias. According to the present invention, an extract is considered soluble if at least 15% by weight of the extract is virtually completely dissolved in the solvent at room temperature or with heating, if necessary.

According to the present invention, it is possible to provide standardized dry extracts exhibiting a defined release in which the weight ratio of the non-volatile extract phase to the carrier is preferably in a range of from 1:10 to 1:0.25, especially from 1:5 to 1:0.6, more preferably from 1:3 to 1:0.7.

If the ratio of extract to carrier is chosen too high, the binding of the extract to the carrier is not sufficient, and thus, optimum release of the active components is not provided.

For the preparation of tablets, effervescent tablets, film tablets, coated tablets, drinking tablets, granules or capsules, per se known further auxiliaries and/or additives are optionally added to the medicinal plant dry extracts or their precursors, the fluid extracts. Thus, when tablets are prepared, the auxiliaries and/or additives may preferably be selected from binders, lubricants, fillers, emulsifiers, wetting agents, transition agents and/or disintegrants.

Fluid extracts are preferably employed. To these extracts is added the carrier material, optionally at elevated temperature. Subsequently, the fluid extract is concentrated to dryness at elevated temperature and/or under vacuum. Fluid extracts within the meaning of the present invention include spissum or dry extracts which are prepared according to per se known methods and redissolved in part or completely using suitable solvents.

The concentration to dryness may also be effected, for example, by spray-drying according to per se known methods or with usual technical equipment, such as spray-dryers or fluidized-bed granulators.

The fluid extracts may be prepared in a simple way by extracting the medicinal plants or the corresponding parts thereof in a suitable solvent. The solvent is preferably selected from acetone, chloroform, ethyl acetate and $C_1$–$C_4$ alcohols, their mixtures with one another and with water. Especially preferred solvents are methanol, ethanol and 2-propanol and their water-free or water-containing mixtures, and especially ethanol/water mixtures. The extraction may be effected in a per se known manner by percolation or multi-step stirring or vortex extraction at room temperature or elevated temperature. In addition to the solvents mentioned, extraction with supercritical carbon dioxide can similarly be employed for the preparation of the raw extracts.

Then, with addition of the carrier and optionally with increasing the temperature and/or under vacuum, the solvent of the extract is removed, and the extract is concentrated to dryness to give a solid or semisolid residue.

EXAMPLES

Example 1

5 kg of Saint-John's-wort dry extract (extractant ethanol, content: 0.3% dianthrones, calculated as total hypericin) was dissolved or suspended with 2 kg of polyethylene glycol (MW 4000). After the polyethylene glycol had dissolved, the alcoholic phase was concentrated in vacuo. A semisolid to solid residue formed.

The composition contained 300 mg of Saint-John's-wort dry extract and 200 mg of the polyethylene glycol.

Example 2

By analogy with Example 1, a tablet was prepared from 40 mg of ginkgo dry extract (1:50) and 80 mg of the polyethylene glycol.

Example 3

By analogy with Example 1, a tablet was prepared from 40 mg of ginkgo dry extract (1:50) and 110 mg of polyvinyl pyrrolidone (Kollidon® 25, corresponding to a K value of 25).

Example 4

By analogy with Example 1, a tablet was prepared from 50 mg of *Passiflora spissum* (4-5:1) and 130 mg of the polyethylene glycol.

Example 5

By analogy with Example 1, a tablet was prepared from 50 mg of *Passiflora spissum* (4-5:1) and 120 mg of the polyvinyl pyrrolidone as used in Example 3.

Example 6

By analogy with Example 1, a tablet was prepared from 300 mg of Saint-John's-wort dry extract and 330 mg of the polyethylene glycol.

Example 7

By analogy with Example 1, a tablet was prepared from 150 mg of Saint-John's-wort dry extract and 190 mg of polyvinyl alcohol (MW 28,000 to 40,000).

Example 8

By analogy with Example 1, a tablet was prepared from 80 mg of Crataegus dry extract (4-7:1) and 190 mg of the polyvinyl pyrrolidone as used in Example 3.

Example 9

By analogy with Example 1, a tablet was prepared from 80 mg of Crataegus dry extract (4-7:1) and 100 mg of the polyethylene glycol.

Example 10

By analogy with Example 1, a tablet was prepared from 4 mg of agnus-castus dry extract and 20 mg of the polyvinyl pyrrolidone as used in Example 3.

Example 11

By analogy with Example 1, a tablet was prepared from 320 mg of sabal-fructus extract and 330 mg of the polyethylene glycol.

Example 12

By analogy with Example 1, a tablet was prepared from 320 mg of sabal-fructus extract and 370 mg of the polyvinyl pyrrolidone as used in Example 3.

Example 13

1 kg of dry extract from Cimicifuga rootstock (extractant ethanol) was dissolved or suspended with 5 kg of polyethylene glycol (MW 4000). After the polyethylene glycol had dissolved, the alcoholic phase was concentrated in vacuo. A semisolid to solid residue formed.

The composition of the tablet was 10 mg of dry extract from Cimicifuga rootstock and 50 mg of the polyethylene glycol.

Example 14

By analogy with Example 1, a tablet was prepared from 300 mg of artichoke (Cynara) leaf dry extract and 350 mg of polyvinyl pyrrolidone (Kollidon® 25, corresponding to a K value of 25).

Example 15

By analogy with Example 1, a tablet was prepared from 300 mg of valerian root dry extract (ethanolic extract) and 300 mg of the polyvinyl pyrrolidone as used in Example 2.

Example 16

By analogy with Example 1, granules were prepared using 330 mg of sabalfructus extract and 550 mg of the polyvinyl pyrrolidone as used in Example 2.

Example 17

By analogy with Example 1, 40 mg of ginkgo dry extract (1:50), 20 mg of the polyvinyl pyrrolidone as used in Example 2 and 200 mg of Ac-di-sol® (sodium salt of an intramolecularly cross-linked carboxymethylcellulose) were used to prepare a solid extract which was then processed into a tablet.

Example 18

By analogy with Example 1, a capsule was prepared using 80 mg of Crataegus dry extract (4-7:1), 25 mg of the polyvinyl pyrrolidone as used in Example 2 and 200 mg of Ac-di-sol®.

Example 19

By analogy with Example 1, 40 mg of ginkgo dry extract (1:50), 40 mg of the polyethylene glycol as used in Example 13 and 200 mg of Ac-di-sol® were used to prepare an extract which was then processed into a tablet.

Example 20

By analogy with Example 1, a capsule was prepared using 150 mg of Hypericum extract, 30 mg of the polyvinyl pyrrolidone as used in Example 2 and 200 mg of Ac-di-sol®.

Example 21

By analogy with Example 1, 210 mg of kava spissum extract (57.1% pyrone content) (corresponding to 120 mg of pyrones), 650 mg of Ac-di-sol® and 70 mg of the polyvinyl pyrrolidone as used in Example 2 were processed into a tablet.

Example 22

By analogy with Example 1, 210 mg of kava spissum extract as used in Example 21, 660 mg of Ac-di-sol® and 75 mg of polyvidone acetate were used to prepare an extract which was then processed into a tablet.

Example 23

By analogy with Example 1, 150 mg of Hypericum extract, 70 mg of the polyvinyl pyrrolidone as used in Example 2 and 1450 mg of sodium hydrogencarbonate were used to prepare a dry extract which was then pressed into an effervescent tablet together with 10 mg of Aspartam®, 60 mg of a polyethylene glycol having a molecular weight of 6000, 2150 mg of citric acid and 50 mg of lemon flavor.

Example 24

By analogy with Example 1, 40 mg of ginkgo dry extract (1:50), 25 mg of the polyvinyl pyrrolidone as used in Example 2 and 1450 mg of sodium hydrogencarbonate were used to prepare a dry extract which was then pressed into an effervescent tablet together with 10 mg of Aspartam®, 60 mg of a polyethylene glycol having a molecular weight of 6000, 2150 mg of citric acid and 50 mg of lemon flavor.

All the above mentioned examples of tablets and granules share the use of conventional auxiliaries for tablets and granules as well as the use of disintegrants, fillers, lubricants or binders.

Process conditions for determining release rates:

According to the regulations of DAB 10 V.5.4 (release of active substances from solid oral dosage forms), the following conditions were used with a blade stirrer apparatus: 900 ml of 0.1 M HCl, 100 rpm, release time 45 min. In all cases of Examples 1 to 24, excellent release rates were obtained with respect to the speed and degree of release.

What is claimed is:

1. An orally administerable medicinal plant dry extract comprising:
    a medicinal plant extract wherein the medicinal plant is sabalfructus (palmetto fruit), Passiflora, chaste-tree (*Vitex agnus-castus*), ginkgo, nettle extract, holy thistle extract, valerian, Cimicifuga root or rootstock, Cynara, or a combination thereof;
    a first carrier, wherein the first carrier is a polyethylene glycol having a molecular weight of at least 1000, polyvinyl alcohol, polyvidone acetate, polyvinyl pyrrolidone, or a combination thereof; and
    at least one second carrier, wherein the second carrier is insoluble in alcohol, insoluble in water, or swellable in water, and solid at room temperature,
    wherein the plant extract is in a microdisperse form, semisolid form, solid solution form, or a combination thereof, and optionally comprises auxiliaries, additives, or a combination thereof.
2. The extract according to claim 1, wherein the weight ratio of the second carrier to the first carrier is from 30:1 to 1:1.
3. The extract according to claim 1, wherein the weight ratio of the non-volatile extract components to the carrier is from 1:10 to 1:0.25.
4. The extract according to claim 1, wherein the auxiliary or additive is a binder, lubricant, filler, emulsifier, wetting agent, disintegrant, or a combination thereof.
5. The extract according to claim 1, in the form of capsules, tablets, granules, and lozenges.
6. The extracts according to claim 1, wherein the weight ratio of the second carrier to the first carrier is from 10:1 to 3:1.
7. The extract according to claim 1, wherein the weight ratio of the non-volatile extract components to the carrier is from 1:5 to 1:0.6.
8. The extract according to claim 1, wherein the weight ratio of the non-volatile extract components to the carrier is from 1:3 to 1:0.7.
9. The tablet according to claim 5, wherein the tablet is an effervescent tablet, film tablet, drinking tablet, or coated tablet.
10. The extract according to claim 1, wherein the polyethylene glycol has a molecular weight of 4000.
11. The extract according to claim 1, wherein the polyvinyl alcohol has a molecular weight from 28,000 to 40,000.
12. The extract according to claim 1, wherein the second carrier is alkaline earth metal carbonate, alkali earth metal carbonate, crosslinked carboxymethylcellulose, or a combination thereof.
13. An orally adminsterable medicinal plant dry extract, comprising a plant extract, a first carrier, and a second carrier, wherein the medicinal plant is Hypericum, and the non-volatile phase of the extract is bound in a microdisperse form, in the form of a semisolid or solid solution, or a combination thereof to the first carrier wherein the first carrier is a polyethylene glycol, polyvinyl alcohol, polyvidone acetate, polyvinyl pyrrolidone, or combinations thereof, optionally having auxiliaries, additives, or a combination thereof.
14. The extract according to claim 13, wherein the second carrier is insoluble in alcohol, insoluble in water, or swellable in water, and solid at room temperature.
15. The extract according to claim 13, wherein the carrier is alkaline earth metal carbonate, alkali earth metal carbonate, crosslinked carboxymethylcellulose, or a combination thereof.

16. The extract according to claim 13, wherein the polyethylene glycol has a molecular weight of at least 1000.

17. The extract according to claim 13, wherein the weight ratio of the second carrier to the first carrier is from 30:1 to 1:1.

18. The extract according to claim 13, wherein the weight ratio of the non-volatile extract components to the first carrier is from 1:10 to 1:0.25.

* * * * *